US009113632B2

(12) United States Patent
Vandenberg et al.

(10) Patent No.: US 9,113,632 B2
(45) Date of Patent: *Aug. 25, 2015

(54) FUNGICIDAL COMPOSITIONS FOR TURF TREATMENT AND IMPROVEMENT

(71) Applicant: BAYER CROPSCIENCE LP, Research Triangle Park, NC (US)

(72) Inventors: Ed Vandenberg, Guelph (CA); Richard Rees, Chapel Hill, NC (US)

(73) Assignee: BAYER CROPSCIENCE LP, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/749,433

(22) Filed: Jan. 24, 2013

(65) Prior Publication Data

US 2013/0137738 A1 May 30, 2013

Related U.S. Application Data

(63) Continuation of application No. 12/761,144, filed on Apr. 15, 2010, now Pat. No. 8,377,850.

(60) Provisional application No. 61/178,711, filed on May 15, 2009.

(51) Int. Cl.
| | |
|---|---|
| *A01N 31/02* | (2006.01) |
| *A01N 47/28* | (2006.01) |
| *A01N 55/02* | (2006.01) |
| *A01N 37/50* | (2006.01) |
| *A01N 43/653* | (2006.01) |
| *A01N 47/38* | (2006.01) |
| *A01N 43/50* | (2006.01) |

(52) U.S. Cl.
CPC ............... *A01N 55/02* (2013.01); *A01N 37/50* (2013.01); *A01N 43/50* (2013.01); *A01N 43/653* (2013.01); *A01N 47/38* (2013.01)

(58) Field of Classification Search
CPC .................................................... A01N 37/02
USPC ................................................. 504/142, 148
See application file for complete search history.

(56) References Cited

U.S. PATENT DOCUMENTS

| | | |
|---|---|---|
| 5,336,661 A | 8/1994 | Lucas |
| 5,506,250 A | 4/1996 | Gouot et al. |
| 5,599,804 A | 2/1997 | Mudge |
| 5,643,852 A | 7/1997 | Lucas et al. |
| 8,377,850 B2 * | 2/2013 | Vandenberg et al. ......... 504/142 |
| 2005/0181949 A1 | 8/2005 | Norton et al. |
| 2006/0293188 A1 | 12/2006 | Norton et al. |
| 2008/0096843 A1 | 4/2008 | Lee et al. |
| 2009/0170918 A1 | 7/2009 | Wolf |
| 2011/0144173 A1 | 6/2011 | Vandenberg |

FOREIGN PATENT DOCUMENTS

| | | |
|---|---|---|
| CN | 1180298 A | 4/1998 |
| CN | 101262762 A | 9/2008 |
| DE | 25 11 077 | 9/1976 |
| EP | 1563734 | 8/2005 |
| JP | 6-279162 | 10/1994 |
| JP | 8-208410 | 8/1996 |
| JP | 2003221576 | 8/2003 |
| JP | 2005225878 | 8/2005 |
| JP | 2009-511612 | 3/2009 |
| WO | 9632011 A2 | 10/1996 |
| WO | 2007045066 | 4/2007 |
| WO | WO2008119439 A2 | 10/2008 |

OTHER PUBLICATIONS

Chinese Office Action dated Apr. 2, 2013 for Chinese Patent Application No. 201080020663.X.
Golob CT, Johnston WJ.; Evaluation of Fungicides From Bayer to Control Pink and Gray Snow Mold on Putting Greens in Idaho and Washington 2007-2008.
International Search Report of PCT/US2010/31239 Dated June 17, 2010.
International Preliminary Report of PCT/US2010/031239 Dated November 15, 2011.

* cited by examiner

*Primary Examiner* — Paul Zarek
(74) *Attorney, Agent, or Firm* — Miles & Stockbridge P.C.

(57) ABSTRACT

The present invention relates to novel compositions comprising: a fungicide that inhibits mitochondrial respiration at the QoI site (QoI inhibitor), a contact fungicide, a demethylation inhibitor, and pigments, which are highly suitable for controlling unwanted phytopathogenic fungi. Moreover, the fungicidal compositions are able to control mold and fungus infection in grasses and in particular turf grasses.

14 Claims, No Drawings

FUNGICIDAL COMPOSITIONS FOR TURF TREATMENT AND IMPROVEMENT

CROSS REFERENCE TO RELATED APPLICATIONS

The present application is a continuation of U.S. application Ser. No. 12/761,144, filed on Apr. 15, 2010, which claims priority to U.S. Provisional Application No. 61/178,711, filed on May 15, 2009, the entire contents of each are herein incorporated by reference in their entireties.

FIELD

This application describes fungicidal compositions that control mold and fungus infection in grasses, in particular turf grasses. More specifically, the compositions comprise a fungicide that inhibits mitochondrial respiration at the QoI site (QoI inhibitor), a contact fungicide, a demethylation inhibitor, and pigments.

BACKGROUND

Fine turf grass species are grown on golf course greens, fairways and tee boxes, as well as turf farms and many other locations. In northern regions, such as Canada and the northern United States, which are subject to temperate climates in the late summer and early fall and snow conditions in late fall and early winter certain moulds such as dollar spot, *Sclerotinia homeocarpa*, and snow molds, such as *Microdochium nivale, Typhula incarnata* and *Typhula ishikariensis*, represent a chronic problem for turf grass growers.

If left untreated in the late summer and fall, turf grass is predisposed to damage caused by *Sclerotinia homeocarpa* in the late summer and fall and the snow molds in late fall and over winter to spring. *S. homeocarpa* attacks most turf grasses grown in the South. Bent grass, common and hybrid bermuda grass and zoysia are most susceptible to *S. homeocarpa* attacks. The dollar spot disease occurs from spring through fall, and is most active during moist periods of warm days (about 70° F. to about 85° F.) and cool nights (about 60° F.) in the spring, early summer and fall.

Where the mold infection is extensive, the recovery of the turf grass can be delayed well into the growing season and seriously affect the ability of the turf grass to recover, leaving areas of dead patches. Further, turf grasses weakened or damaged by these molds are extremely slow to recover in the spring and are often invaded by undesirable opportunistic weedy grass species such as creeping bent grass (*Agrostis palustris*) and annual bluegrass (*Poa annua*).

A typical snow mold prevention program requires a mold inhibiting fungicide to be applied to turf grass prior to permanent winter snow cover. Typical programs consist of three applications prior to permanent snow cover and an additional application after the snow cover is gone in the spring. Several commercial fungicide products have been approved for use against dollar spot and snow mould species.

COMPASS (trifloxystrobin; (aE)-a(methoxyimino)-2-[[[(E)-1-[3-(trifluoromethylphenyflethylidine]-amino[oxy[methyl[benzenacetic acid methyl ester) is an aromatic dioxime fungicide which has been approved for the control of leaf spot, *Fusarium* patch and brown patch diseases in turf grass. Trifloxystrobin is a quinone outside inhibitor (QoI) and a member of the class of aromatic dioxime fungicides described in U.S. Pat. No. 5,238,956, the contents of which are incorporated in their entirety herein.

ROVRAL GREEN GT (iprodione; 3-(3,5-dichlorophenyl)-N-(1-methylethyl)-2,4-dioxo-1-imidazolidinecaboximide) is a dicarboximide fungicide for pink snow mold control at a rate of 250 ml/100 m$^2$ and for gray snow mould control at a rate of 375 ml/100 m$^2$. Iprodione is a member of the class of 3-phenyl hydantoin compounds described in U.S. Pat. No. 3,755,350, the contents of which are incorporated in their entirety herein. The effectiveness of iprodione to control the spread of snow mold in turf grasses (especially the gray snow molds *T. incarnata* and *T. ishikariensis*) is highly variable due to the varying amounts of fungus inoculums, the varying length of snow cover under which snow mould inoculums thrive and the varying winter temperatures that exist across the country from year to year. Thus, in order to effectively control against a spectrum of snow moulds a relatively high dose may be required as well as multiple applications.

Phthalocyanines are known pigments having many applications, such as pigments for inks and coatings and even for turf grass paints. See, for example, DE 2,511,077, the contents of which are incorporated in their entirety herein, and JP 03/221576, the contents of which are incorporated in their entirety herein. Copper phthalocyanine has been used, but only in combination with certain other active ingredients, for enhancing turf quality. For example, U.S. Pat. No. 5,599,804, the contents of which are incorporated in their entirety herein, describes a method of combating fungi and enhancing turf quality in turf grass by applying in specific ratios certain phthalocyanines in combination with phosphorous acid or an alkaline earth metal salt thereof or with certain monoester salts of phosphorous acid. U.S. Pat. No. 5,643,852, the contents of which are incorporated in their entirety herein, describes a method of enhancing turf quality in turf grass by applying in specific ratios certain phthalocyanines in combination with (i) phosphorous acid or an alkaline earth metal salt thereof or certain monoester salts of phosphorous acid and (ii) certain ethylene bisdithiocarbamate contact fungicides. U.S. Pat. No. 5,336,661, the contents of which are incorporated in their entirety herein, describes a method of treating bent grass and enhancing turf quality by applying in specific ratios (i) certain monoester salts of phosphorous acid and (ii) a metallic ethylene bisdithiocarbamate contact fungicide. This patent also describes a specific composition containing a combination of aluminum tris(O-ethylphosphonate) (fosetyl-al) and a manganese-zinc ethylene bisdithiocarbamate complex (mancozeb) used in a form (FORE fungicide) believed to have contained an unknown amount of the phthalocyanine compound Pigment Blue 15.

It has been unexpectedly discovered that compositions comprising any two of the following three fungicides: (i) a QoI inhibitor fungicide, (ii) a contact fungicide, and (ii) a demethylation inhibitor; and certain pigments show superior mold control abilities than compositions with similar fungicides but without the pigments.

DETAILED DESCRIPTION

QoI inhibitor fungicides include trifloxystrobin. Contact fungicides include fludioxinil, iprodione and chlorothalonil, and iprodione and fludioxinil involve signal transduction in their mode of action. Demethylation inhibitors include triticonazole and propiconazole. Pigments include phthalocyanines such as Green pigment (Green 7) and Pigment Blue 15.

To determine the superiority of various compositions comprise a QoI inhibitor fungicide, a contact fungicide, and a demethylation inhibitor with pigments over a composition containing three classes of fungicides but without pigments, trials were conducted at the following sites: 1. University of Massachusetts, Vermont Site; 2. University of Wisconsin, Sentry Site; 3. University of Wisconsin, Iron Mountain Site; 4. University of Wisconsin, Champion Mich. Site; 5. University of Wisconsin, Edina Minn. Site; 6. Oregon State University, Sun River Site; 7. Washington State University, McCall Site; 8. Washington State University, Chewelah Site; and 9. Washington State University Pullman Site.

A general procedure for the application of the compositions described is as follows. Treatment plots were, for example, 6 feet×7 feet with three replications in a randomized complete-block design. Treatments were applied from late-October to mid-November. In several instances, the compositions were applied at 80 GPA with a bicyclewheeled $CO_2$ pressurized (40 psi) sprayer with 11008 flat fan TeeJet nozzles.

Several sites have intermittent snow cover throughout the winter with periods of continuous snow cover. Once the snow melted, or is mechanically removed, individual plots were evaluated for pink (*M. nivale*) and/or gray (*Typhula* spp.) snow mold disease severity (% area infected) and turf grass quality (rated on a scale of 1 to 9, with 9 being excellent).

Table 1 shows the effect of a composition containing differing amounts of a QoI inhibitor fungicide (trifloxystrobin), a contact fungicide (iprodione), a demethylation inhibitor (triticonazole) and a pigment (phthalocyanine Green pigment) in comparison with a standard combination of three classes of fungicides combined for snow mold control that does not contain any pigments (INSTRATA, manufactured by SYNGENTA) on Turf Quality (TQ) or Turf Color (TC). The scale is from 1 to 9 with 1=poor and 9=excellent. INSTRATA was used as a control because it is a snow mold product that has three classes of fungicides but does not have any pigments.

TABLE 1

| Treatment[b] | Pink and Gray snow mold sites[a] | | | | | | | | | Mean of all Sites |
|---|---|---|---|---|---|---|---|---|---|---|
| | 1 | 2 | 3 | 4 | 5 | 6 | 7 | 8 | 9[d] | |
| Untreated | 5.7 | 4.5 | 6 | 3.3 | 6.3 | 1.5 | 2.3 | 1 | 1.7 | 4 |
| (A + B + C): 4 oz/1000 sq ft + (C + D): 0.85 oz/1000 sq ft | 7 | 8 | 7.8 | 7.8 | 8.3 | 6.5 | 5.7 | 5 | 4.7[e] | 7 |
| (A + B + C): 5 oz/1000 sq ft + (C + D)[c]: 0.85 oz/1000 sq ft | 7 | 8 | 7.8 | 7.8 | 8 | 7.3 | 5.7 | 6.3 | 4.7[f] | 7 |
| INSTRATA[c]: 9.3 oz/1000 sq ft | 5.7 | 6.8 | 6 | 6.3 | 7 | 4.3 | 5.7 | 5.7 | 4 | 6 |

[a]Sites:
1. University of Massachusetts, Vermont site;
2. University of Wisconsin, Sentry Site;
3. University of Wisconsin, Iron Mountain Site;
4. University of Wisconsin, Champion MI Site;
5. University of Wisconsin, Edina MN Site;
6. OSU, Sun River Site;
7. Washington State University McCall Site;
8. Washington State University Chewelah Site;
9. Washington State University Pullman Site.
[b]A = trifloxystrobin; B = iprodione; C = Phthalocyanine Green pigment (Green 7); D = triticonazole (3 lb ai/gal).
[c]INSTRATA = commercial standard without pigment (propiconazole + fludioxinil + chlorothalonil).
[d]Pink snow mold site.
[e](A + B + C): 4 oz/1000 sq ft.
[f](A + B + C): 5 oz/1000 sq ft.

A composition comprising A+B+C+D is the equivalent of INSTRATA+a pigment. In other words, using such a composition, a direct comparison can be made to demonstrate the superior effects of a composition containing the three classes of fungicides with a pigment vs. a composition containing only the three classes of fungicides (i.e., without a pigment). The results show that in every site where the composition containing the three classes of fungicides with a pigment is used, the TQ and TC are superior to INSTRATA. This means that the turf recovers better and looks better using the composition containing the three classes of fungicides with a pigment vs. INSTRATA.

The results from site 9, in which a composition comprising two fungicides (A+B) and C show that the composition of two fungicides and a pigment is at least as good as INSTRATA, if not slightly better. This is surprising because INSTRATA has three fungicides (but no pigment). In other words, an effect similar to using three fungicides can be achieved by the use of two fungicides and a pigment.

Table 2 shows the effect of a composition containing differing amounts of a QoI inhibitor fungicide (trifloxystrobin), a contact fungicide (iprodione), a demethylation inhibitor (triticonazole) and a pigment (phthalocyanine Green pigment) in comparison with INSTRATA on percentage disease infestation by site. The scale is from 1 to 9 with 1=poor and 9=excellent.

TABLE 2

| Treatment | Pink and Gray snow mold sites | | | | | | | | | Mean of all Sites |
|---|---|---|---|---|---|---|---|---|---|---|
| | 1 | 2 | 3 | 4 | 5 | 6 | 7 | 8 | 9[d] | |
| Untreated | 56.7 | 76.3 | 43.8 | 96.3 | 17.5 | 73.8 | 28.3 | 73.3 | 51.7 | 58 |
| (A + B + C): 4 oz/1000 sq ft + (C + D): 0.85 oz/1000 sq ft | 11.7 | 0 | 0 | 3 | 0 | 6.3 | 5.3 | 6.7 | 0[e] | 4 |
| (A + B + C): 5 oz/1000 sq ft + (C + D): 0.85 oz/1000 sq ft | 8.7 | 0 | 0 | 1.3 | 5 | 8.8 | 2 | 1.7 | 2.7[f] | 3 |
| INSTRATA: 9.3 oz/1000 sq ft | 2.3 | 0.5 | 0 | 13.8 | 0 | 21.3 | 0 | 0 | 1.7 | 4 |

[d] Pink snow mold site.
[e] (A + B + C): 4 oz/1000 sq ft.
[f] (A + B + C): 5 oz/1000 sq ft.

The results in Table 2 show that the composition containing the three classes of fungicides with a pigment cures about the same percentage of disease infestation as INSTRATA. In other words, the composition disclosed is as effective as INSTRATA in killing mold. The superior benefits of a composition additionally comprising a pigment, such as a phthalocyanine, include better recovery of the turf after the winter, during the spring green up; better health of the turf; and better aesthetics (the turf looks visual better).

Once again, same results are seen at site 9 as in Table 2: a composition of two fungicides and a pigment is surprisingly as effective as one with three fungicides.

Therefore, compositions comprising two fungicides and a pigment are within the scope of this disclosure. Such compositions include a QoI inhibitor fungicide with a contact fungicide, and a pigment; a QoI inhibitor fungicide, a demethylation inhibitor, and a pigment; a contact fungicide, a demethylation inhibitor, and a pigment.

The QoI inhibitor fungicide, contact fungicide, the demethylation inhibitor; and the pigment may be in any ratio within the composition. Examples of suitable ratios are shown in Table 3.

TABLE 3

| Component (g/L) | Lower end | | | | | | | | | Higher end |
|---|---|---|---|---|---|---|---|---|---|---|
| QoI inhibitor fungicide | 1 | 2 | 3 | 4 | 5 | 6 | 7 | 8 | 9 | 10 |
| Contact fungicide[g] | 50 | 50 | 50 | 50 | 50 | 50 | 50 | 50 | 50 | 50 |
| Demethylation inhibitor | 12 | 16 | 20 | 25 | 29 | 33 | 37 | 41 | 45 | 50 |
| Pigment | 20 | 22 | 24 | 26 | 29 | 32 | 34 | 36 | 38 | 40 |

[g] the amount of the contact fungicide is kept constant as a reference point.

Other exemplary compositions of trifloxystrobin, iprodione, and phthalocyanine Green pigment include those shown in Table 4, suspended in water.

TABLE 4

| Component (g/L) | Lower end | | | | | | | | | Higher end |
|---|---|---|---|---|---|---|---|---|---|---|
| Trifloxystrobin | 1.30 | 1.34 | 1.37 | 1.40 | 1.44 | 1.47 | 1.50 | 1.54 | 1.57 | 1.60 |
| Iprodine | 21.2 | 21.6 | 22.2 | 22.6 | 23.2 | 23.6 | 24.2 | 24.6 | 25.2 | 25.6 |
| Phthalocyanine | 5.5 | 5.6 | 5.7 | 5.8 | 5.9 | 6.0 | 6.1 | 6.2 | 6.3 | 6.4 |

Table 5 shows the superior effects of a composition containing 1.47 g/L of trifloxystrobin, 29.41 g/L of iprodione, 3.14 g/L of triticonazole, and 6 g/L of phthalocyanine over a commercially available solution of INSTRATA. The four-component composition and INSTRATA were applied to a bent grass/*Poa* plot at Westmount Golf & Country Club in Kitchener, Ontario, Canada.

TABLE 5

| Composition applied | Amount applied (mL/m$^2$) | Total disease area (%) | TQ |
|---|---|---|---|
| None (untreated) | 0 | 83 | 1 |
| Trifloxystrobin: 1.47 g/L + Iprodine: 29.41 g/L + Triticonazole: 3.14 g/L + Phthalocyanine: 6 g/L | 100 133 177.5 | 0 0 0 | 8.7 9 9 |
| INSTRATA | 300 | 2 | 6.6 |

As the results show, application of the four-component composition of trifloxystrobin, iprodione, triticonazole, and phthalocyanine is superior to INSTRATA. Not only does the four-component composition provide better disease control than INSTRATA (as measured by the % area affected)—0% vs. 2% but the TQ is better 8.7 to 9 vs. 6.6. Additionally, excellent results can be achieved by using significantly lower amounts of the composition (100 mL/100 m$^2$ to 177.5 mL/m$^2$) vs. INSTRATA (300 mL/m$^2$). This is significant not only from an environmental perspective in that fewer chemicals are applied to the soil but also from an economic perspective in lower costs.

It should be understood that this disclosure is intended to cover compositions comprising, consisting essentially of, and consisting of at least two fungicides selected from the group consisting of a QoI inhibitor fungicide, a contact fungicide, and a demethylation inhibitor; and a phthalocyanine pigment. Without being bound by theory, it is believed that the various fungicides act in synergy with the pigment, thereby resulting in the superior effects observed.

The disclosure also is intended to cover methods of treating various turf species by application of the described compositions. Turf species that the described compositions can be used on include creeping bent grass, colonial bent grass, annual bluegrass, other *Poa* species of grasses, Bermuda grass, Rye grass, and other common grasses of golf courses, sport fields and sod farms.

The described compositions may be applied to healthy or diseased turfs. Prophylactic application to healthy turf may be helpful in preventing turf diseases. Application to turf containing one or more turf diseases is helpful in treating the one or more turf diseases. The turf diseases that the described compositions can treat include dollar spot, brown patch, anthracnose, gray leaf spot, and diseases of golf courses, sport fields, and sod farms. The described compositions are also helpful in improving turf quality after snow cover release in spring.

What is claimed is:

1. A synergistic composition, comprising:
   (i) at least two fungicides selected from the group consisting of a QoI inhibitor fungicide, a contact fungicide, and a demethylation inhibitor; and
   (ii) a phthalocyanine pigment
   wherein the QoI inhibitor fungicide is trifloxystrobin, the contact fungicide is selected from fludioxinil, iprodione, or chlorothalonil, and the demethylation inhibitor is selected from triticonazole or propioconazole.

2. The synergistic composition of claim 1, wherein: the QoI inhibitor fungicide is trifloxystrobin, the contact fungicide is iprodione, the demethylation inhibitor is triticonazole, and the pigment is phthalocyanine green pigment (Green 7).

3. A method for improving turf quality after snow cover release in spring, comprising:
   administering a synergistic composition, the synergistic composition comprising:
   (i) at least two fungicides selected from the group consisting of a QoI inhibitor fungicide, a contact fungicide, and a demethylation inhibitor; and
   (ii) a phthalocyanine pigment
   wherein the QoI inhibitor fungicide is trifloxystrobin, the contact fungicide is selected from fludioxinil, iprodione, or chlorothalonil, and the demethylation inhibitor is selected from triticonazole or propioconazole,
   to turf grass.

4. The method of claim 3, wherein: the QoI inhibitor fungicide is trifloxystrobin, the contact fungicide is iprodione, the demethylation inhibitor is triticonazole, and the pigment is phthalocyanine green pigment (Green 7).

5. The synergistic composition of claim 1, comprising a QoI inhibitor fungicide and a contact fungicide.

6. The synergistic composition of claim 1, comprising a contact fungicide and a demethylation inhibitor.

7. The synergistic composition of claim 1, comprising a QoI inhibitor fungicide and a demethylation inhibitor.

8. The synergistic composition of claim 1, comprising a QoI inhibitor fungicide which comprises trifloxystrobin.

9. The synergistic composition of claim 1, comprising a contact fungicide selected from fludioxinil, iprodione, or chlorothalonil.

10. The synergistic composition of claim 1, comprising a demethylation inhibitor selected from triticonazole or propioconazole.

11. The synergistic composition of claim 1, comprising a QoI inhibitor fungicide, a contact fungicide, and a demethylation inhibitor.

12. The synergistic composition of claim 11, wherein the QoI inhibitor fungicide comprises trifloxystrobin, the contact fungicide comprises fludioxinil, iprodione, or chlorothalonil, and the demethylation inhibitor comprises triticonazole or propioconazole.

13. The synergistic composition of claim 11, wherein the QoI inhibitor fungicide comprises trifloxystrobin, the contact fungicide comprises iprodione, and the demethylation inhibitor comprises triticonazole.

14. The synergistic composition of claim 5, wherein the QoI inhibitor fungicide comprises trifloxystrobin and the contact fungicide comprises iprodione.

* * * * *